(12) United States Patent
Harding et al.

(10) Patent No.: US 7,187,436 B2
(45) Date of Patent: Mar. 6, 2007

(54) MULTI-RESOLUTION INSPECTION SYSTEM AND METHOD OF OPERATING SAME

(75) Inventors: Kevin George Harding, Niskayuna, NY (US); Joseph Benjamin Ross, Cincinnati, OH (US)

(73) Assignee: General Electric Company, Niskayuna, NY (US)

( * ) Notice: Subject to any disclaimer, the term of this patent is extended or adjusted under 35 U.S.C. 154(b) by 318 days.

(21) Appl. No.: 10/813,149

(22) Filed: Mar. 30, 2004

(65) Prior Publication Data

US 2005/0219519 A1    Oct. 6, 2005

(51) Int. Cl.
*G01N 21/00* (2006.01)
(52) U.S. Cl. .................. 356/237.2; 356/237.4
(58) Field of Classification Search ............ None
See application file for complete search history.

(56) References Cited

U.S. PATENT DOCUMENTS

| 4,659,220 | A | 4/1987 | Bronte et al. | |
|---|---|---|---|---|
| 4,764,969 | A | 8/1988 | Ohtombe et al. | |
| 4,998,005 | A | 3/1991 | Rathi et al. | 219/121.83 |
| 6,122,046 | A * | 9/2000 | Almogy | 356/237.2 |
| 6,522,777 | B1 | 2/2003 | Paulsen et al. | 382/154 |
| 6,870,169 | B2 * | 3/2005 | Obara et al. | 250/492.2 |

FOREIGN PATENT DOCUMENTS

| DE | 101 04 425 A1 | 9/2001 |
|---|---|---|
| EP | 0 398 781 A | 11/1990 |

OTHER PUBLICATIONS

Yamazaki, I. et al.; "Microscopy and Analysis of Wafer Particles Using a Semiconductor Defect Review System"; Hitachi Review, Hitachi Ltd., Tokyo, Japan, vol. 45, No. 1, Feb. 1, 1996, pp. 7-10.

* cited by examiner

*Primary Examiner*—Michael P. Stafira
(74) *Attorney, Agent, or Firm*—Fletcher Yoder

(57) ABSTRACT

A multi-resolution inspection system and method of operation. The system may comprise a first scanning system having a first resolution, wherein the first scanning system is operable to perform a first resolution scan of a surface area of an object to identify a location of a surface abnormality in the object. The system may also comprise a second scanning system having a second resolution, the second resolution being smaller than the first resolution. The second scanning system is operable to receive the location of the surface abnormality from the first scanning system and to automatically perform a second resolution scan of a defined region of the object around the location of the surface abnormality.

29 Claims, 6 Drawing Sheets

MULTI-RESOLUTION INSPECTION SYSTEM AND METHOD OF OPERATING SAME

BACKGROUND

The invention relates generally to the field of inspection techniques and, more particularly, to automated inspection techniques employed in a manufacturing environment.

In a manufacturing environment, it may be desirable to inspect a work piece either before, during, or after the work piece is manufactured to ensure that the work piece is manufactured without defects. In some cases, a visual inspection of the work piece is sufficient to determine if the work piece has any defects, such as scratches, cracks, or other surface abnormalities. However, in other cases, the size of a defect may be so small that a person making a visual inspection of the work piece will not be able to see the defect.

As a result, various types of inspection systems and methods have been developed to facilitate the inspection of work pieces in a manufacturing environment. In general, these inspection techniques are used to inspect precision parts to identify any errors or surface defects in the work pieces. For example, inspection systems are used to measure the characteristics of a work piece to check for any shape deformations. In addition, inspection systems have been used to measure the dimensions of critical features of the work pieces in order to verify that the dimensions of the work piece are correct. In certain applications, the size of a surface defects may be so small that a high-resolution scanning system is needed to enable the surface defect to be seen and identified. Automated inspection systems have been developed that are capable of automatically scanning a work piece and obtaining the desired information.

However, scanning the entire surface area of a work piece with a high-resolution scanning system may greatly increase the inspection time and, therefore, the production time of the work piece. In addition, the inspection time increases with the size of the work piece. Thus, performing a high-resolution scan of a large work piece may take a considerable amount of time. Therefore, it would be desirable to have a technique that enables a work piece to be scanned for surface defects in a more efficient manner. More specifically, it would be desirable to have a technique that enabled small defects in large work pieces to be identified in a more efficient manner.

BRIEF DESCRIPTION

Briefly, in accordance with one aspect of the present invention, an inspection system comprising a first scanning system having a first resolution and a second scanning system having a second resolution is provided. The first scanning system is operable to perform a first resolution scan of a surface area of an object to identify a location of a surface abnormality in the object. The second resolution is a higher resolution than the first resolution. The second scanning system is operable to receive the location of the surface abnormality from the first scanning system and to automatically perform a scan of a defined region of the object around the location of the surface abnormality identified by the first scanning system.

In accordance with another aspect of the present invention, a method of inspecting a part is provided. The method comprises directing a first scanning system to automatically perform a first scan of an object using a first resolution to identify a location of a surface abnormality. The method may also comprise coupling the location of the surface abnormality to a second scanning system and directing the second scanning system to automatically perform a second scan of a defined portion of the object at the location of the possible surface defect using a higher resolution than the first resolution.

DRAWINGS

These and other features, aspects, and advantages of the present invention will become better understood when the following detailed description is read with reference to the accompanying drawings in which like characters represent like parts throughout the drawings, wherein.

Figure 1:
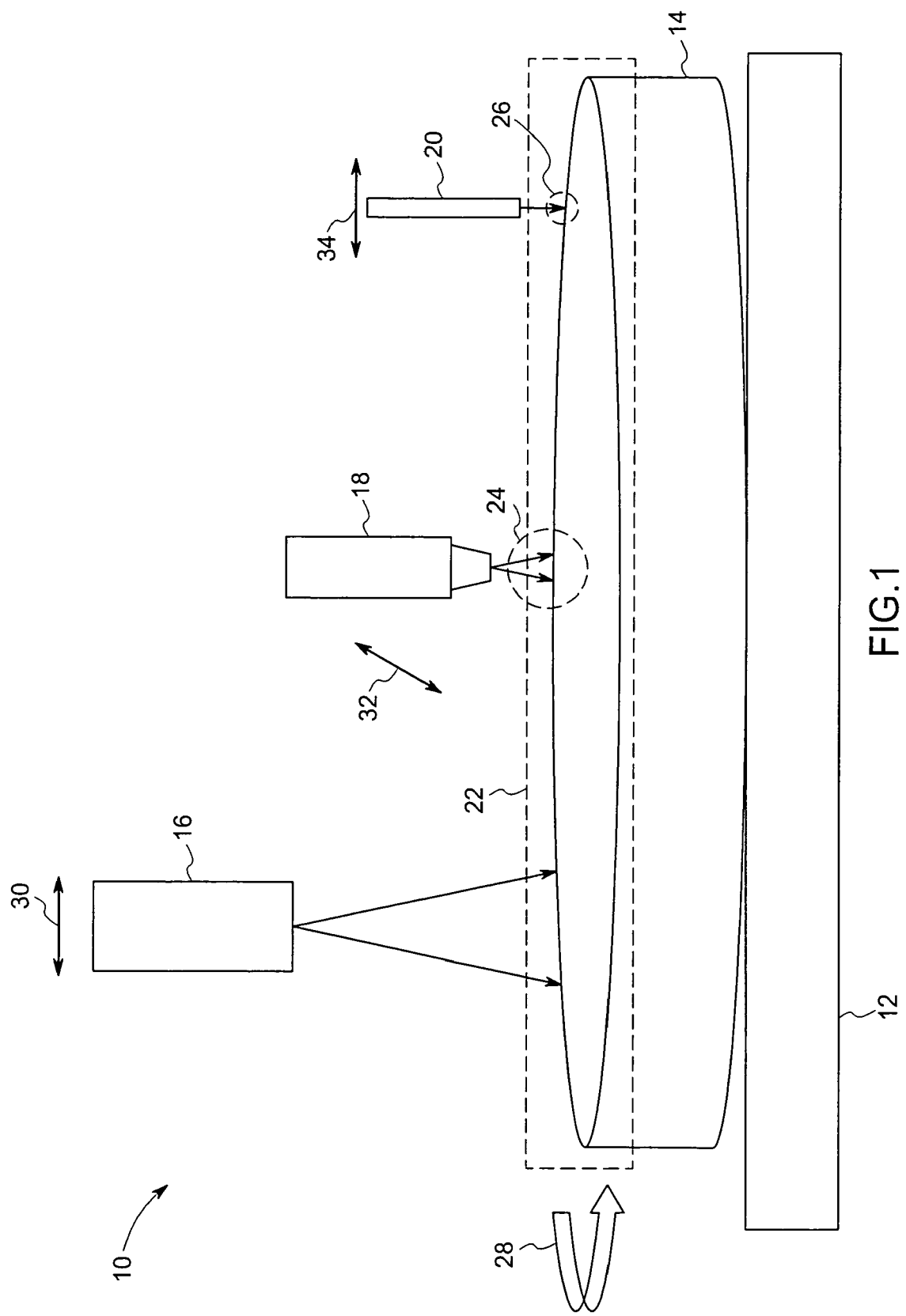
FIG. 1 is a diagrammatical representation of an exemplary inspection system for inspection of precision parts, in accordance with aspects of the present technique.
Figure 7:
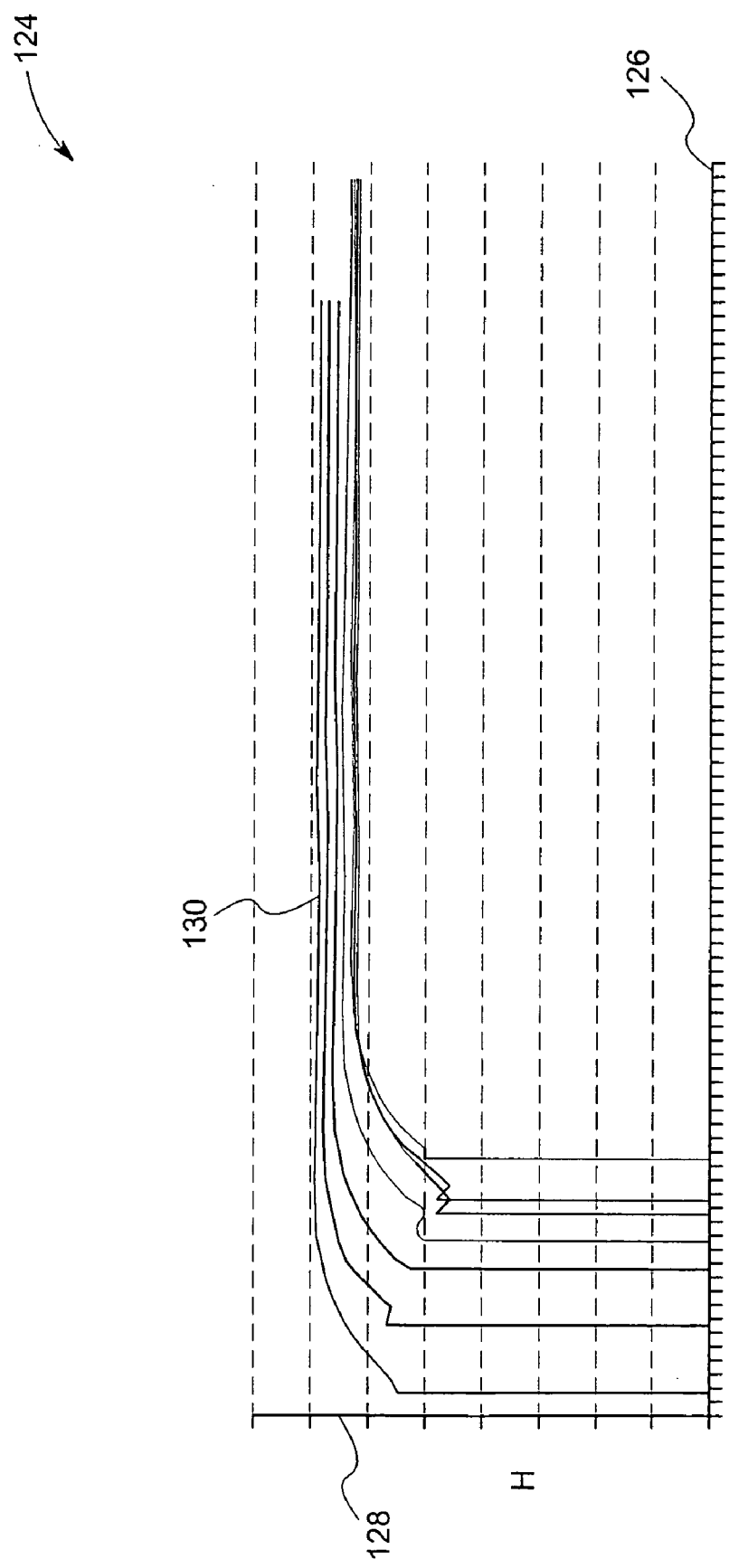
Figure 8:
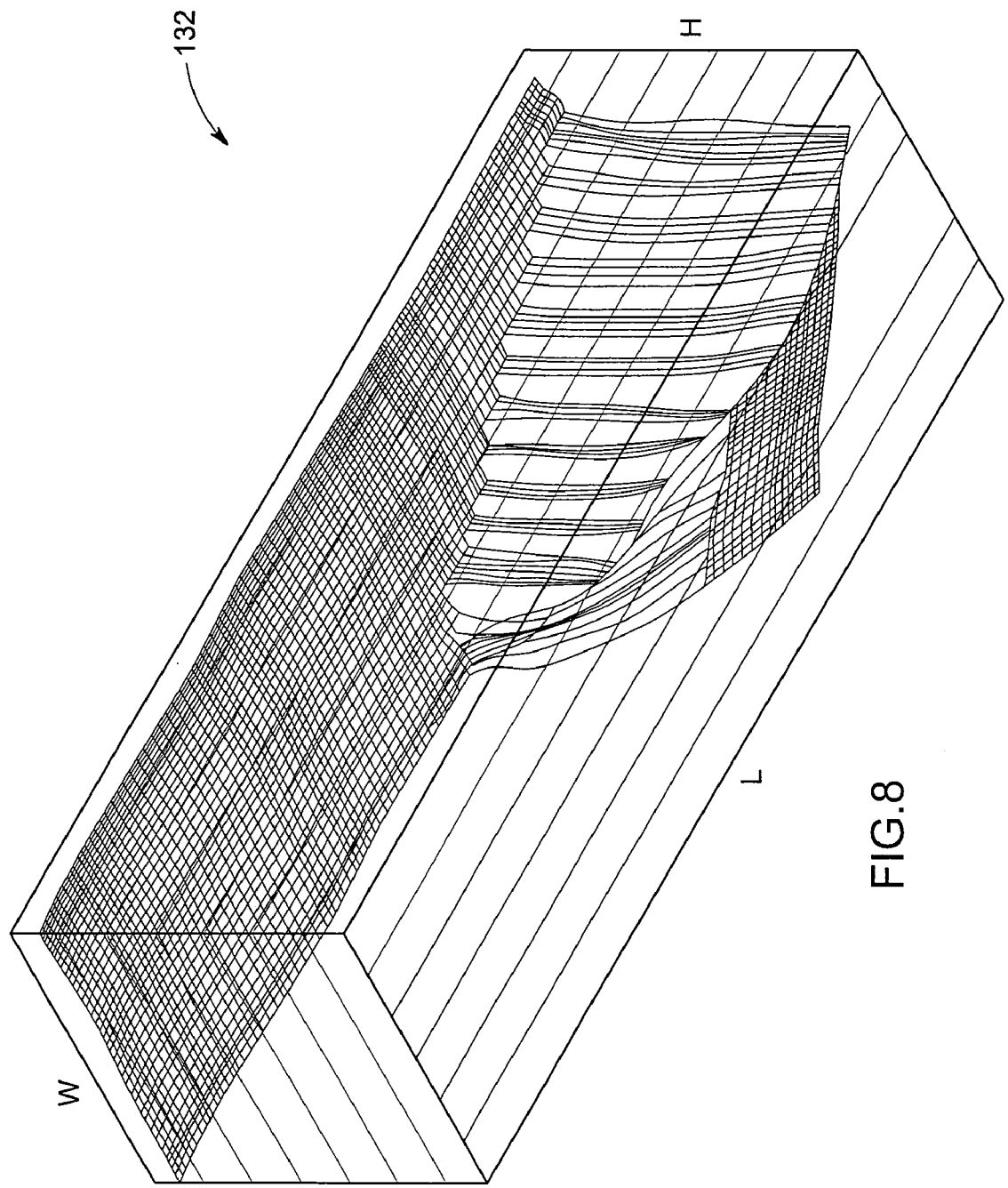

FIG. 7 is a graphical representation of a set of two-dimensional data obtained from a region having a possible surface defect by the inspection system of FIG. 1, in accordance with aspects of the present technique; and FIG. 8 is a graphical representation of a set of three-dimensional data from a region having a possible surface defect obtained by the inspection system of FIG. 1, in accordance with aspects of the present technique.

DETAILED DESCRIPTION

Referring now to FIG. 1, an automated multi-resolution inspection system, represented generally by reference numeral 10, is illustrated. The multi-resolution inspection system 10 comprises a part fixture 12 operable to support a work piece 14. In addition, the illustrated embodiment of the multi-resolution inspection system 10 comprises a first scanning system 16, a second scanning system 18, and a third scanning system 20 configured to inspect the work piece 14. However, a fewer number of scanning systems may be used in the multi-resolution inspection system 10.

The first scanning system 16 is operable to perform a first scan of a surface area 22 of the work piece 14 to identify the location of any surface abnormalities in the work piece 14. The surface area 22 may be the entire visible surface area of the work piece 14 or a smaller portion of the work piece 14. The first scanning system 16 has a resolution that enables it to identify surface abnormalities of a specified size. In the illustrated embodiment, the first scanning system 16 comprises a machine vision system that is operable to provide a basic analysis of shapes, sizes, and positions to enable the first scanning system 16 to locate any surface abnormalities that may be surface defects. In addition, the first scanning system 16 is operable to provide the second scanning system 18 with the location of the surface abnormalities. The fixture may rotate the work piece 14, as represented by the arrow 28, so that a first scan of the entire surface area 22 of the work piece 14 is performed by the first scanning system 16. Additionally, the first scanning system 16 may be moved horizontally, as represented by the arrow 30, to facilitate the scanning of the surface of the work piece 14 by the first scanning system 16.

In the illustrated embodiment, the second scanning system 18 receives the location of the surface abnormality from the first scanning system 16 and performs a second scan of a defined region 24 of the work piece 14 encompassing a surface abnormality identified by the first scanning system 16. If multiple surface abnormalities are identified, the second scanning system 18 performs a separate scan of each surface abnormality. The second scanning system 18 has a higher resolution than the resolution of the first scanning system 16. The higher resolution provided by the second scanning system enables the system or an operator to determine whether the surface abnormality is an acceptable feature or a defect. Preferably, the second scanning system 18 has a resolution sufficient to give the second scanning system 18 the ability to measure a specific surface feature to a level of ten times the tolerance for a defect.

The second scanning system 18 is operable to provide two-dimensional data for each defined region 24 around each surface abnormality. In the illustrated embodiment, the second scanning system 18 also comprises a machine vision system. However, other types of scanning systems may be used, such as a probe or an interferometer. The second scanning system 18 also may be operable to perform a three-dimensional scan of the work piece 14, thereby enabling the second system 18 to provide three-dimensional data, in addition to two-dimensional data. In the illustrated embodiment, the second scanning system 18 is configured to move in a radial direction, as represented by the arrow 32, to enable the second scanning system 18 to scan the defined area 24.

In the illustrated embodiment, a third scanning system 20 is provided to obtain three-dimensional data for the surface abnormality, such as an image of the surface abnormality and the parameters of the surface abnormality. The location of each surface abnormality may be provided to the third scanning system by either the first scanning system 16 or the second scanning system 18. The third scanning system 20 is configured to move in a direction, represented by arrow 34, to obtain the dimensional characteristics of the surface abnormality in the defined region 26 around the location of a surface abnormality. Examples of three-dimensional scanning systems 20 include an inductive probe, a passive probe, and a laser probe. However, other types of scanning systems may be used.

Figure 2:
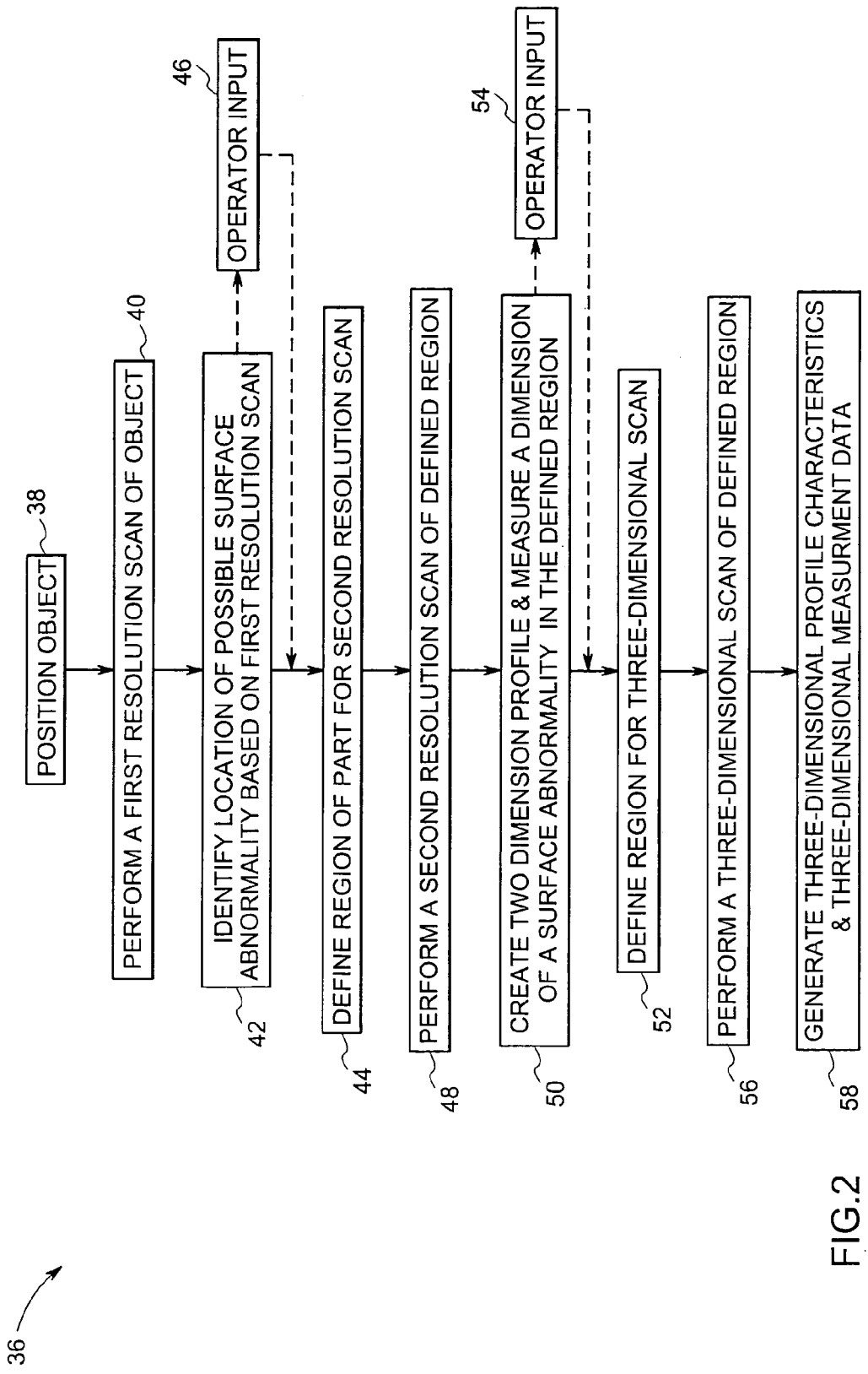
FIG. 2 is a flow chart illustrating a method of inspecting an object using the system of FIG. 1, in accordance with aspects of the present technique.

Referring generally to FIGS. 1 and 2, a method of performing an automated inspection of a work piece using the multi-resolution inspection system 10 of FIG. 1 is illustrated in FIG. 2, and represented generally by reference numeral 36. Initially, the work piece 14 is positioned on the fixture 12 to enable the system 10 to automatically inspect the work piece 14, as represented by block 38.

The method of inspection comprises performing a first resolution scan of the work piece 14 automatically using the first scanning system 16, as represented by block 40. The scan may be performed over the entire surface area of the work piece 14 or over a smaller area of the work piece 14. The first scanning system 16 is used to identify the location of a surface abnormality, such as a surface defect, as represented by block 42. The method may also comprise defining a region around each possible surface defect for performing a second scan with the second scanning system 18, as represented by block 44. The region of the object to be scanned with the second scanning system 18 is defined to be large enough to encompass the surface abnormality, but is smaller than the surface area 22 of the work piece 14 scanned by the first scanning system 16. A user may be able to define the size of the surface abnormality that will be identified by the system 10 as the location of a possible surface defect, as represented by block 46.

The method of inspection also comprises performing a second scan of each of the defined regions of the work piece 14 around a surface abnormality automatically using the second scanning system 18, as represented by block 48. The resolution of the second scanning system 18 is a higher resolution than the resolution of the first scanning system 16. The second resolution scan may be used to provide an image of each defined region 24, two-dimensional data representative of each defined region 24, and/or a graphical representation of each defined region, as represented by block 50. A user may evaluate the image, the two-dimensional data, and the graphical representation obtained from the second scanning system 18 and determine whether the surface abnormality is an actual surface defect or is an acceptable abnormality. The efficiency of the inspection process is improved by scanning only those regions of the work piece 14 that have been identified as being abnormal or having a possible surface defect with the higher resolution second scanning system 18. The second canning system 18 is not used to scan large portions of the work piece 14 that do not have surface abnormalities.

The method also comprises defining a region 26 around a possible surface defect for performing a three-dimensional scan with the third scanning system 20, as represented by block 52. The region 26 for performing the three-dimensional scan may be the same region as the region 24 scanned by the second scanning system 18. However, based on the results of the second scan, the number of regions to be scanned with the third scanning system 20 may be a lesser number than the number of regions 24 scanned by the second scanning system 18. A user may provide the parameters to define the regions 26 of the work piece 14 to be scanned with the third scanning system 20, as represented by block 54.

The inspection method may also comprise performing a three-dimensional scan of the defined regions 26 of the work piece 14, as illustrated in block 56. The three-dimensional scan may be used to provide an image of the defined region 26, three-dimensional data representative of the defined region 26, and/or a graphical representation of the region 26 of the surface abnormality, as represented by block 58. A user may evaluate the image, the three-dimensional data, and the graphical representation and determine whether the surface abnormality is an actual surface defect or an acceptable feature.

Figure 3:
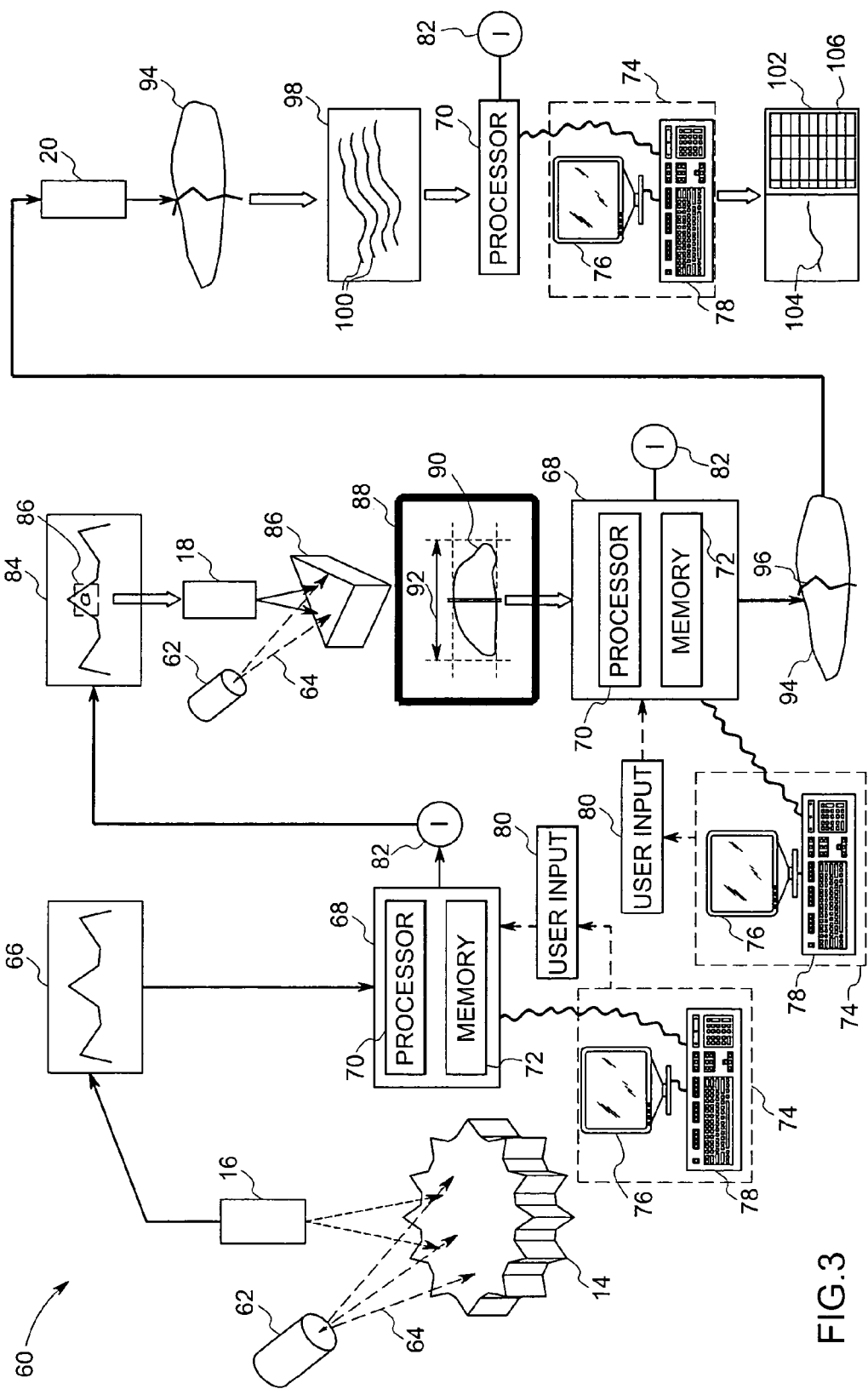
FIG. 3 is a diagrammatical view of an inspection process using the system of FIG. 1 and the method of FIG. 2, in accordance with aspects of the present technique.

Referring generally to FIG. 3, a diagrammatical representation of an automated inspection performed by the inspection system setup of the multi-resolution inspection system of FIG. 1 using the method of FIG. 2 is illustrated, and represented generally by reference numeral 60. In a presently contemplated configuration, the first scanning system 16 is positioned over the work piece 14 for performing a first resolution scan of the work piece 14. Further, an illumination source 62 may be provided to facilitate the performance of the first resolution scan of the work piece 14.

The illumination source 62 may project light 64 to illuminate the surface 22 of the work piece 14. In the illustrated embodiment, the first scanning system 16 comprises a machine vision system. The machine vision system comprises a machine vision camera that converts visual images into a digital signal to enable the first scanning system 16 to perform a basic analysis of shapes, sizes and positions of the features of the work piece 14.

However, scanning systems other than a machine vision system may be used. For example, the first scanning system 16 may be a charge-coupled device camera. In addition, in the illustrated embodiment, the first scanning system 16 is a low-resolution scanning system having a resolution of a few thousands of an inch.

The first scanning system 16 is operable to generate a first resolution image 66 of the work piece 14. The first resolution image 66 may be used by the system 10 to establish feature locations relative to other features and to locate possible defect areas. The first resolution image 66 is then received by control circuitry 68 that is coupled to the first scanning system 16. In the illustrated embodiment, the control circuitry 68 includes a processor 70 and a memory device 72. The memory device 72 stores a reference image of the surface area of the work piece 14. The processor 70 receives the first resolution image 66 of the object and compares the first resolution image 66 with the reference image stored in the memory device 72. When the difference between the scanned image 66 and the reference image exceeds a defined value or size, the first scanning system 16 identifies the location of the first resolution image 66 as the location of a surface abnormality and, thus, a possible surface defect.

Additionally, an operator interface 74, such as a computer, is coupled to the control circuitry 68 to enable a user to control the operation of the first scanning system 16. The first scanning system 16 enables a first resolution image 66 of the work piece 14 to be visible to a user of the system 16 via a monitor 76. A user interface 78 may be provided to enable a user to provide an input 80 to the control circuitry 68, such as a definition of the size of a defect or surface abnormality that will be identified by the system 16 as a surface abnormality or possible surface defect. An interface 82 is provided to couple the location of a surface abnormality to the second scanning system 18.

The second scanning system 18 receives the location 84 of an area of the work piece 14 for performing a second resolution scan 86 from the first scanning system 16. The region 86 of the work piece 14 around the location of the surface abnormality is identified by the control circuitry 68 for the second resolution scan. The second scanning system 18 automatically performs a second resolution scan of the defined region 86 of the object around the location of the surface abnormality. It should be noted again that, the second scanning system 18 has a higher resolution than the first scanning system 16. An illumination source 62 may be provided with the second scanning system 18 to facilitate the scanning of the defined region 86 of the work piece 14. As with the first scanning system 16, the second scanning system 18 in the illustrated embodiment comprises a machine vision system. However, the second scanning system 18 may use other types of devices, such as a digital comparator or an interferometer. In addition, the second scanning system 18 is a high-resolution scanning system. For example, the second scanning system 18 may have a resolution of 0.000001 inch, as opposed to a resolution of a few thousands of an inch of the first scanning system 16. The second scanning system 18 is operable to provide two-dimensional data for the surface abnormality in the defined region 86. As noted above, the second scanning system 18 may also be operable to provide three-dimensional data for the surface abnormality.

The second resolution scan 88 obtained by the second scanning system 18 enable the system 18 provide a two-dimensional profile map 90 of the defined region 86 of the work piece 14. In addition, the second resolution scan 88 may also enable the system 18 to provide a measurement of a dimension 92 of the surface abnormality in the defined region 86 of the work piece 14. The dimension 92 may be the height or depth of the surface abnormality. Alternatively, the dimension 92 may be the width or length of the surface abnormality.

Further, the second scanning system 18 may be coupled to the control circuitry 68 used by the first scanning system 16. However, the second scanning system 18 may also have its own control circuitry 68. In the illustrated embodiment, the control circuitry 68 identifies a region to be scanned by the three-dimensional scanning system 20. As with the first scanning system, the control circuitry 68 compares the characteristics of the two-dimensional profile of the defined region of the object with a reference two-dimensional profile stored in the memory device 72. The control circuitry 68 is operable to identify a region 94 containing a surface abnormality or possible defect 96 for performing a three-dimensional scan with the third scanning system 20.

The third scanning system 20 is operable to perform a three-dimensional scan of the identified surface abnormality 96 to produce a three-dimensional image 98 of the surface abnormality within the defined region 94 of the work piece 14. The third scanning system 20 is operable to generate a series of three-dimensional profiles 100 within the defined region 94 of the object. The third scanning system 20 is coupled to the processor 70 to process the three-dimensional measurement data 102. Additionally, the measurement data 102 is visible to a user via a monitor 76 of a computer 74. The three-dimensional scan data 102 available to the user of the system may include a graphical representation 104 of the three-dimensional scan of the surface abnormality 96 and various dimensional parameters 106 of the surface abnormality 96. The dimensional parameters 106 may include the height, width, and depth of the surface abnormality 96.

Figure 4:
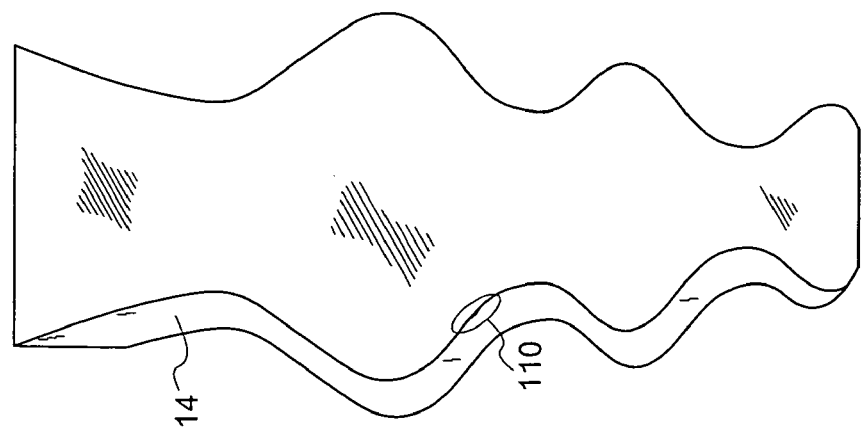
FIG. 4 is a view of an image of an object showing a surface abnormality obtained from a first scanning system of the inspection system of FIG. 1, in accordance with aspects of the present technique.

Referring generally to FIG. 4, an example of an image 108 of the work piece 14 generated from the first scanning system 16 is illustrated. The image 108 may enable a user to identify the location of a possible defect 110.

Figure 5:
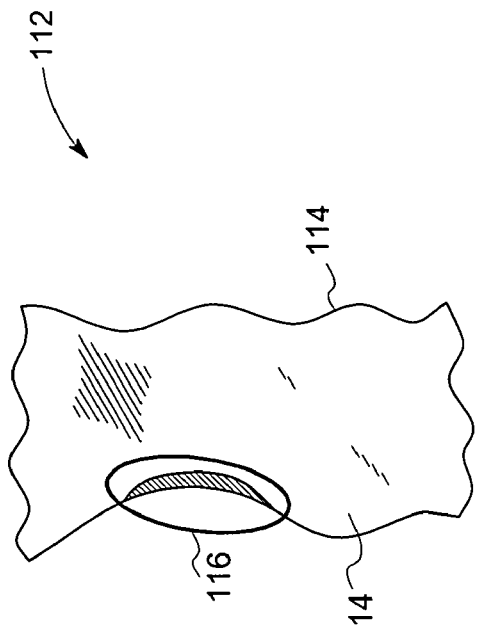
FIG. 5 is a view of a two-dimensional image of the object showing the surface abnormality obtained from a second scanning system of the inspection system of FIG. 1, in accordance with aspects of the present technique.

Referring generally to FIG. 5 a two-dimensional image 112 obtained from the second scanning system is illustrated. The two-dimensional image 112 provides a higher resolution image 116 of the surface abnormality within the surface area 114 of the work piece 14. As shown, the resolution of the image 112 generated from the second scanning system 18 is higher than the resolution of the image 108 obtained from the first scanning system 16, illustrated in FIG. 4. In general, the resolution of the image 112 is at least ten times smaller than the tolerance of the feature. The image 112 is generated by scanning a small region of the work piece 14 surrounding the location of the surface abnormality.

Figure 6:
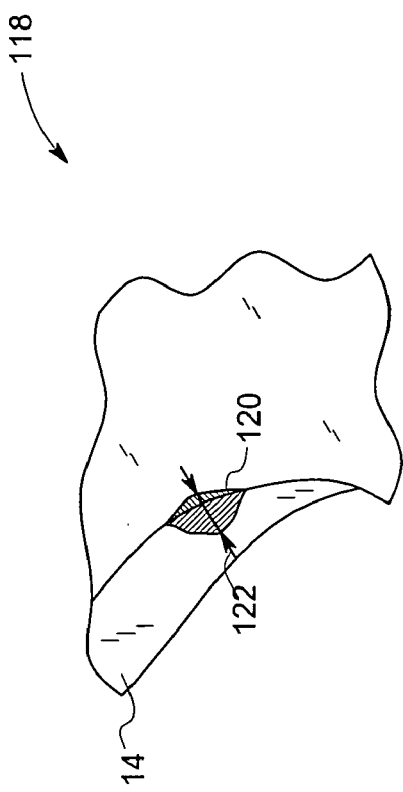
FIG. 6 is a view of a three-dimensional image of the object obtained from the second scanning system of the inspection system of FIG. 1, in accordance with aspects of the present technique.

FIG. 6 illustrates an example of a three-dimensional image 118 of a possible surface defect in the work piece 14. The three-dimensional image 118 may be generated by the second scanning system 18. The three-dimensional image 118 shows the defect or the surface abnormality 120 in the object in a three-dimensional view. Furthermore, the dimensions 122 of the defect 120 may be obtained using the three-dimensional image 118 shown in FIG. 6.

FIG. 7 illustrates a graphical representation 124 of two-dimensional data obtained by the second scanning system 18. The graphical representation has an x-axis 126 and a y-axis 128 that enables a user to define the height "H" and width "W" of the possible defect. The x-axis 126 may represent the width of the surface abnormality 116 and the y-axis may represent the height or the depth of the surface abnormality 116. Alternatively, the x-axis 126 may represent the height or the depth of the surface abnormality 116 and the y-axis 128 may represent the width of the surface abnormality 116. A series 130 of graphs of dimensional data from a plurality of scans is illustrated.

The system 10 may be programmed to identify a work piece 14 as defective if the dimensions of the surface abnormality exceed defined limits programmed into the system 10. Alternatively, an inspector may use the image of the surface abnormality, the dimensional data, and the graphical representation to determine whether the surface abnormality is within acceptable limits or is a defect.

FIG. 8 illustrates a graphical representation 132 of three-dimensional data 132 generated by the inspection system of FIG. 1. The three-dimensional profile 132 may be used to quantitatively measure a small feature, such as of a crack. The three-dimensional graphical representation 132 provides measurement data, such as the height "H", and the width "W", and the length "L", of the defect. As with the data above, an inspector may use the image, the dimensional data, and the graphical representation to determine if the surface abnormality is within acceptable limits or is a defect.

The inspection technique described provides an efficient inspection methodology for inspecting work pieces that require a high-resolution scan to identify a surface defect. The technique utilizes a lower resolution scanning system to perform an initial scan of the work piece to identify locations of possible surface defects. The lower resolution scanning system is operable to scan at a much faster speed than the higher resolution scanning system. This technique enables the higher resolution scanning system to be used only where there is already some indication of a surface abnormality or defect. Please note that the multi-resolution scanning system 10 may be a single scanning device or one or more devices that have the ability to perform different scanning functions. For example, the first scanning system 16 and the second scanning system 18 may be a single scanning device operable to perform scans with different resolutions. Similarly, the second scanning system 18 and the third scanning system 20 may be one device that has the ability to perform a high-resolution two-dimensional scan and a high-resolution three-dimensional scan.

The various aspects of the inspection technique described above may be used in various manufacturing environments. For example, aircraft engines have a number of components that are formed by various manufacturing operations. These components require inspection with a relatively high-resolution system to enable surface defects to be identified. Preferably, these defects are identified early in the manufacturing process, so that defective parts may be corrected or discarded in the early stages of manufacturing. As noted above, the inspection technique described herein enables quantitative characterization of the defects and features efficiently and effectively. This inspection technique also may be used in other applications For example, in the automobile industry the technique may be used for automatically detecting flaws and providing quantitative data of these defects and any other required features of any automobile components or machinery.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A multi-resolution inspection system comprising:
a first scanning system having a first resolution, wherein the first scanning system is operable to perform a first scan of a surface area of an object to identify a location of a surface abnormality in the object; and
a second scanning system having a second resolution, the second resolution being a higher resolution than the first resolution, wherein the second scanning system is operable to receive the location of the surface abnormality from the first scanning system and to define a region of the object around the location of each surface abnormality to automatically scan with the second scanning system.

2. The system of claim 1, wherein the second scanning system defines a specific region around each location of a plurality of surface abnormalities provided by the first scanning system to automatically scan with the second scanning system.

3. The system of claim 1, wherein the region scanned by the second scanning system is smaller in area than the surface area of the object scanned by the first scanning system.

4. The system of claim 1, wherein the first scanning system comprises a machine vision system.

5. The system of claim 1, wherein the second scanning system comprises a machine vision system.

6. The system of claim 1, wherein the second resolution is at least ten times smaller than the first resolution.

7. The system of claim 1, wherein the second resolution is at least ten times smaller than a tolerance for a surface feature to be identified as a defect.

8. The system of claim 1, wherein the second scanning system is operable to provide two-dimensional data representative of the region of the object.

9. The system of claim 1, wherein the second scanning system is operable to provide three-dimensional data representative of the region of the object.

10. The system of claim 9, wherein the second scanning system is operable to provide a three-dimensional graphical representation of the region of the object.

11. The system of claim 1, wherein the first scanning system scans the surface area of the object at a first speed and the second scanning system scans the defined region of the object at a second speed, the first speed being greater than the second speed.

12. The system of claim 1, comprising a third scanning system operable to produce a three-dimensional graphical representation of the defined region of the object.

13. The system of claim 12, wherein the third scanning system comprises a laser scanner.

14. The system of claim 1, wherein the first scanning system is coupled to control circuitry, wherein the control circuitry identifies a surface abnormality by comparing the first resolution scan with a reference image of the surface area of the object.

15. The system of claim 1, wherein the first scanning system enables a user to define the size of a surface variation to direct the first scanning system to identify as a surface abnormality.

16. A method of inspecting a part comprising:
directing a first scanning system to automatically perform a first scan of an object using a first resolution to identify a location of a possible surface defect;
coupling the location of a possible surface defect to a second scanning system; and
directing the second scanning system to automatically perform a second scan of a defined portion of the object at the location of the possible surface defect using a second resolution that is a higher resolution than the first resolution.

17. The method of claim 16, wherein directing the second scanning system comprises directing the second scanning system to produce a two-dimensional representation of the defined region of the object at the location of the possible surface defect.

18. The method of claim 17, comprising establishing a dimensional parameter of the possible defect based on the two-dimensional data and comparing the dimensional parameter to an acceptable tolerance for the dimensional parameter stored in the system, wherein the system automatically identifies the possible defect as a defect when the dimensional parameter exceeds the tolerance for the dimensional parameter.

19. The method of claim 17, comprising scanning the defined region with a third scanning system when the area of the possible defect exceeds the defined area of a defect.

20. The method of claim 19, comprising providing three-dimensional parameters of the defined region of the object.

21. The method of claim 16, wherein directing the second scanning system comprises directing the second scanning system to map a three- dimensional profile of the defined region of the object at the location of the surface defect.

22. The method of claim 16, wherein coupling the location of the surface defect comprises comparing the first resolution scan obtained from the first scanning system with a reference image of the object to identify the location of a possible surface defect.

23. An automated inspection system, comprising:
a first scanning system operable to automatically scan a first surface area of an object using a first scanning resolution to identify a location of a surface abnormality; and
a second scanning system operable to receive the location of the surface abnormality from the first scanning system and to automatically perform a three- dimensional scan of the object at the location of the possible defect.

24. The system of claim 23, wherein the second scanning system has a second scanning resolution that is smaller than the first scanning resolution.

25. The system of claim 24, wherein the second resolution is at least ten times smaller than the first resolution.

26. The system of claim 23, wherein the first scanning system comprises a machine vision system.

27. The system of claim 23, wherein the second scanning system comprises a machine vision system.

28. The system of claim 23, wherein the first scanning system is coupled to control circuitry, wherein the control circuitry identifies the surface abnormality by comparing the first resolution scan with a reference image of the surface area of the object.

29. The system of claim 23, wherein the first scanning system scans the surface area of the object at a first speed and the second scanning system scans the defined region of the object around the location of the surface abnormality at a second speed, the first speed being greater than the second speed.

* * * * *